(12) United States Patent
Shenoy et al.

(10) Patent No.: US 7,531,359 B2
(45) Date of Patent: May 12, 2009

(54) CAVITANDS FOR CHEMICAL VAPOR SENSING

(75) Inventors: Devanand Shenoy, McLean, VA (US); Elias Feresenbet, Allentown, PA (US); Enrico Dalcanale, Parma (IT); Susan Daly, Alexandria, VA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 591 days.

(21) Appl. No.: 11/307,966

(22) Filed: Mar. 1, 2006

(65) Prior Publication Data

US 2007/0036681 A1  Feb. 15, 2007

Related U.S. Application Data

(60) Provisional application No. 60/662,341, filed on Mar. 15, 2005, provisional application No. 60/662,340, filed on Mar. 15, 2005.

(51) Int. Cl.
*G01N 33/00* (2006.01)
*G01N 21/00* (2006.01)
*G01N 21/75* (2006.01)
*G01N 31/22* (2006.01)
*C07D 323/00* (2006.01)

(52) U.S. Cl. .................. 436/104; 436/106; 436/164; 422/57; 422/82.05; 549/348

(58) Field of Classification Search ............... 436/104, 436/106, 164, 181; 422/57, 82.05; 549/348
See application file for complete search history.

(56) References Cited

OTHER PUBLICATIONS

Dalcanale et al., "Molecular dynamics and conformational behaviour of mesogenic resorcinarenes" *Liq. Cryst.*, 27(9), 1161-1169 (2000).
Dalcanale et al., "Selective detection of organic compounds by means of cavitand-coated QCM transducers" *Sensors and Actuators B*, B24-25, 39-42 (1995).

Feresenbet et al., "Optical sensing of the selective interaction of aromatic vapors with cavitands" *Sensors and Actuators*, B97, 211-220 (2004).
Hassan et al., "Kinetic studies of BTEX vapour adsorption onto surfaces of calic-4-resorcinarene films" *Appl. Surf. Sci.*, 182, 49-54 (2001).
Hof et al., "Acetylcholine Recognition by a Deep, Biomimetic Pocket" *Angew. Chem. Int. Ed.*, 42, 3150-3153 (2003).
Huisman et al., "Molecular Recognition by Self-Assembled Monolayers Detected with Surface Plasmon Resonance" *Adv. Mater.*, 8(7), 561-564 (1996).
Lagugné-Labarthet et al., "Orientation of cavitands at sir/water and air/solid interfaces studied by second harmonic generation" *Chem. Phys. Lett.*, 381, 322-328 (2003).
Menozzi et al., "Surface-Confined Single Molecules: Assembly and Disassembly of Nanosize Coordination Cages on Gold (111)" *Chem. Eur. J.*, 10, 2199-2206 (2004).
Nabok et al., "Condensation of organic vapors within nanoporous calixarene thin films" *J. Mater. Chem.*, 10, 189=194 (2000).
Oshovsky et al., "Anion Complexation by Glycocluster Thioureamethyl Cavitands: Novel ESI-MS-Based Methods for the Determination of $K_a$ Values" *Chem. Eur. J.*, 10, 2739-2748 (2004).
Pinalli et al., "Supramolecular Sensors for the Detection of Alcohol" *Angew. Chem. Int. Ed..*, 38(16), 2377-2380 (1999).
Poalesse et al., "Investigation of the Origin of Selectivity in Cavitand-Based Supramolecular Sensors" *Chem. Eur. J.*, 9, 5388-5395 (2003).
Schierbaum et al., "Molecular Recognition by Self-Assembled Monolayers of Cavitand Receptors" *Science*, 265, 1413-1415 (1994).
Shenoy et al., "Effect of Thin Film Processing on Cavitand Selectivity" *Langmuir*, 19(4), 10454-10456 (2003).
Suman et al., "Cavitand-Based Supramolecular Sensors for the Detection of Acetates" *J. Supramol. Chem.*, 2, 97-106 (2002).
Suman et al., "Rational Design of Cavitand Receptors for Mass Sensors" *J. Am. Chem. Soc.*, 125, 12068-12069 (2003).

*Primary Examiner*—Jill Warden
*Assistant Examiner*—Dean Kwak
(74) *Attorney, Agent, or Firm*—John J. Karasek; Joseph T. Grunkemeyer

(57) ABSTRACT

The chemical compound:

-continued
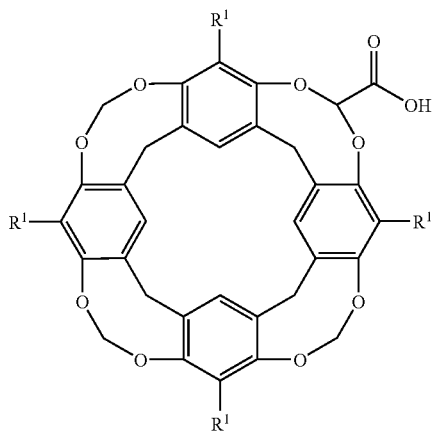
Each $R^1$ is H or $CH_3$. A device for detecting an analyte having: a substrate; a film on the substrate, a flow cell for delivering air containing the analyte to the film, and an apparatus for measuring the refractive index of the film.
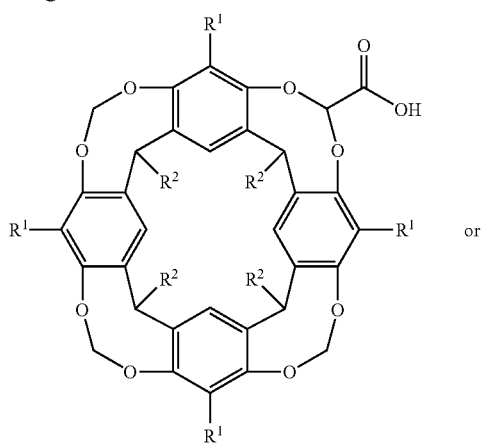
or
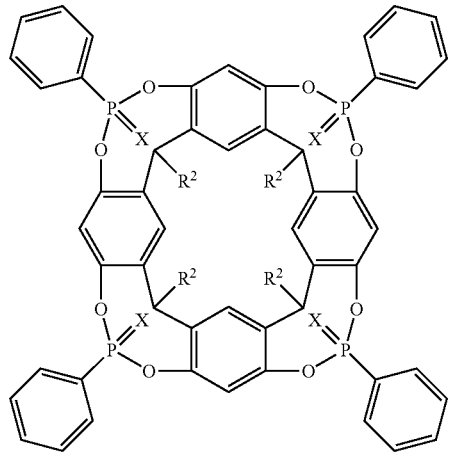
Each $R^2$ is an alkyl group. Each X is O or S.
24 Claims, 10 Drawing Sheets

R = C₅H₁₁

COOH-OUT

R = C₅H₁₁

COOH-IN

R = C₁₁H₂₃

Tiiii[C₁₁H₂₃, H, Ph]

R = C₁₁H₂₃

TSiiii[C₁₁H₂₃, H, Ph]

CAVITANDS FOR CHEMICAL VAPOR SENSING

CROSS REFERENCE TO RELATED APPLICATIONS

This application claims priority to U.S. Provisional Patent Application Nos. 60/662,340 and 60/662,341, both filed on Mar. 3, 2005, and both incorporated herein by reference. U.S. patent application entitled "NEMATIC LIQUID CRYSTAL THIN FILMS FOR CHEMICAL VAPOR SENSING," designated as 97182US2, and filed on the same day as the present application, is incorporated herein by reference.

FIELD OF THE INVENTION

The invention is generally related to cavitand compounds and sensors using cavitands.

DESCRIPTION OF RELATED ART

A problem with current chemical vapor detectors is that they are still prone to false alarms and are relatively bulky causing inconvenience. The problem of false alarms is caused by the limited selectivity and sensitivity of sensing layers for chemical threats and therefore there is a need for new materials with enhanced selectivity and sensitivity.

Cavitands are synthetic organic compounds that contain rigid cavities with well-defined molecular dimensions that can be tailored to interact preferentially with certain types of analytes by fine tuning of weak intermolecular interactions like hydrogen bonding, CH-π interactions, or dipole-dipole interactions. Complexation properties of cavitands with various analytes have been extensively studied in the solid and gas phases, as well as in solution. Thin films of cavitand have been deposited onto substrates using spin-coating, self-assembly and Langmuir-Blodgett deposition. These films have been evaluated for their vapor adsorptivity using quartz crystal microbalance (QCM), ellipsometry, and surface plasmon resonance (SPR).

The major bottleneck in the development of cavitand-based supramolecular sensors is the inability to distinguish specific binding events that occur within the cavity from non-specific dispersion interactions that occur elsewhere within the permeable cavitand layer. The advantage of SPR over other transduction schemes is its increased sensitivity. Unlike some other techniques, SPR can detect vapor interactions with monolayer thin films of cavitand, hence non-specific interactions can be reduced.

BRIEF SUMMARY OF THE INVENTION

The invention comprises a chemical compound comprising the formula. Each $R^1$ is independently selected from H and $CH_3$.

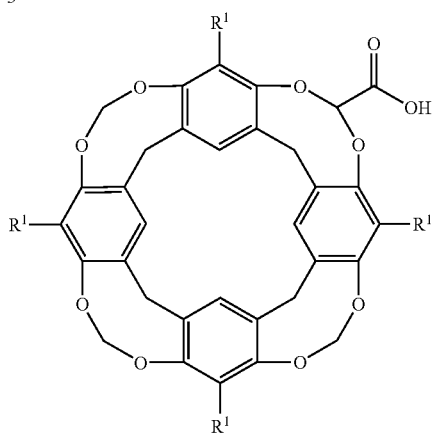

The invention further comprises a device for detecting an analyte comprising: a substrate; a film on the substrate, a flow cell capable of delivering air suspected of containing the analyte to the film, and an apparatus capable of measuring the refractive index of the film. The film comprises one of the following chemical compounds. Each $R^1$ is an independently selected from H and $CH_3$, and each $R^2$ is an independently selected alkyl group. Each X is O or S.

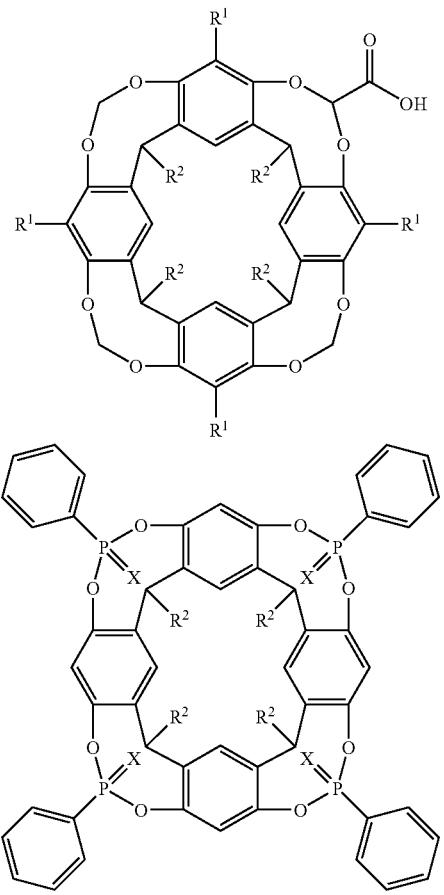

The invention further comprises a method of detecting an analyte comprising:

providing a device comprising the above substrate and film, exposing the film to air suspected of containing the analyte; and measuring a change in the refractive index of the film in response to exposing the film.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
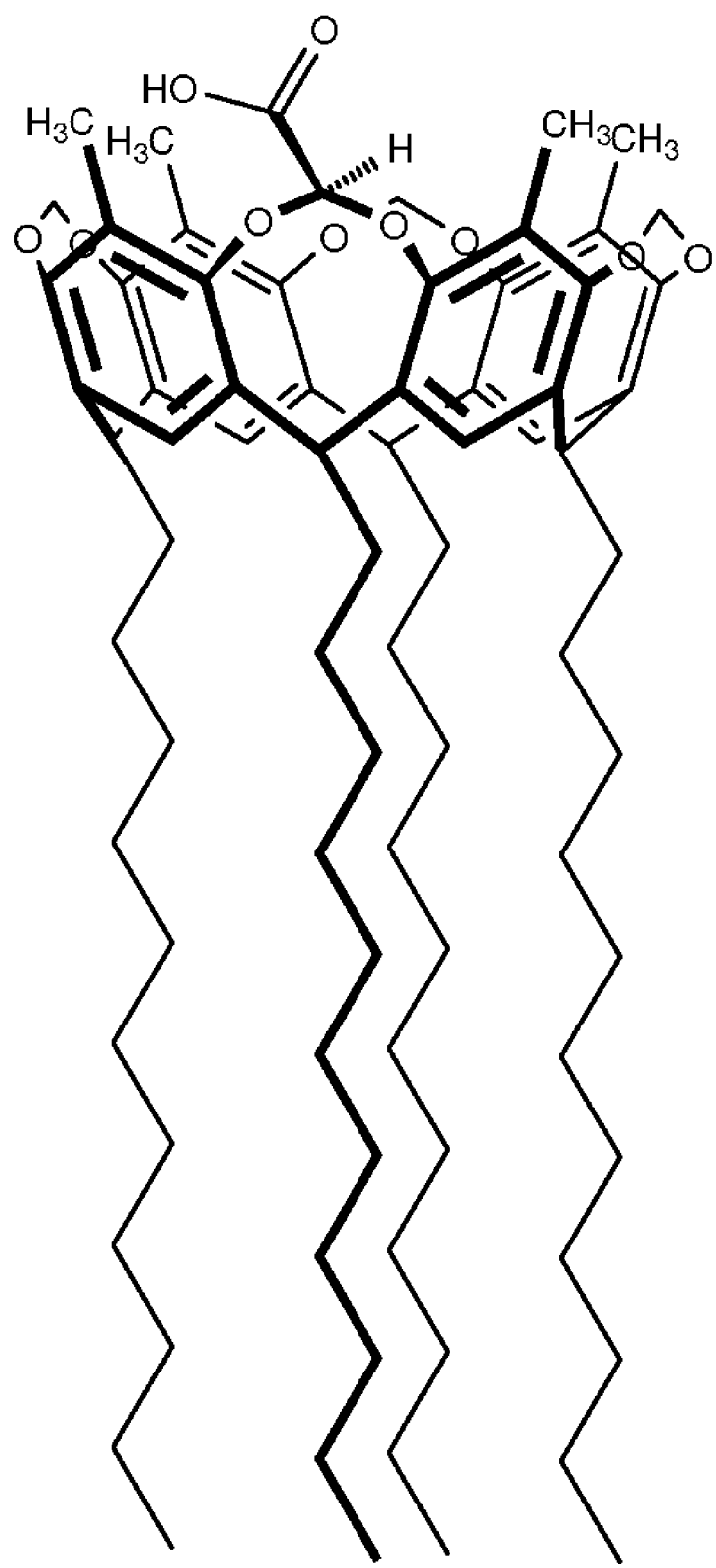
FIG. 1 shows an example cavitand.

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Disclosed are the preparation and chemical-sensing behavior of cavitands specifically designed to interact with organophosphorus vapors. This molecular receptor is a methylene-bridged cavitand with a single hydrogen-bond donating COOH group introduced at the upper rim of the rigid cavity (compound 1). This carboxyl group is expected to hydrogen bond with the P=O group on the organophosphorus molecule. Dimethyl methylphosphonate DMMP may interact more strongly with the COOH containing cavitand than with other types of cavitand films or with a polymeric fluoropolyol-sensing layer. The COOH cavitand may also interact less strongly with contaminating vapors than other types of coatings. Spin-cast layers and LB deposited layers of similar thickness may respond identically to DMMP, however thicker LB films may interact more strongly with DMMP.

Cavitand materials can be used as coatings in chemical vapor detectors. Given that cavity size and molecular interactions dictate the formation of the complex, the analyte is not permanently bound in the cavity after detection. Further, the analyte is not destroyed during detection. Hence, employing the cavitands in a detection system provides a unique opportunity to trap, transport, and release analytes yielding a re-useable sensing platform. Being robust organic compounds, these can be re-used indefinitely. The process used for recycling does not degrade the cavitand. In addition to this clear advantage of the cavitands as a sensing platform, the cavitands have been shown to be extremely robust. Cavitands can withstand high temperatures in experiments where molecular recognition is achieved in the gas phase, e.g. M. Vincenti et al., "Host-guest complexation in the gas phase by desorption chemical ionization mass spectrometry" *J. Am. Chem. Soc.*, 112, 445 (1990), for which particular cavitands have to be evaporated so that they can interact with gas phase analytes and have been demonstrated to withstand temperatures as high as 400° C. in gas phase studies. These compounds do not require special conditions for storage such as in a freezer and do not degrade with time. They can be safely stored at room temperature.

The cavitands sensing platform may by coupled with a highly sensitive transduction technique. Surface plasmon resonance (SPR) provides the capability to transduce the formation of the guest-host complex, i.e. the interaction of chemical agent vapors with the cavitand, at concentrations at the ppb to ppt range.

The chemical compound is a cavitand containing a carboxylic group on one of the upper, bridging methylene groups (COOH). The compound optionally has one to four methyl groups on the phenyl groups. The compound has an "in" and an "out" configuration with regard to the carboxylic group. This group is oriented towards the center of the compound in the "in" conformation, as shown in the left-hand formula below (COOH-IN), or away from the center in the "out" conformation, as shown in the right-hand formula below (COOH-OUT).

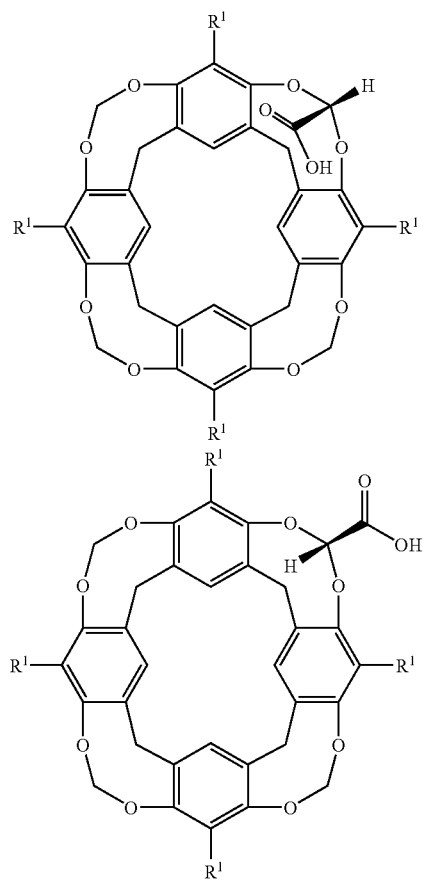

Figure 2:
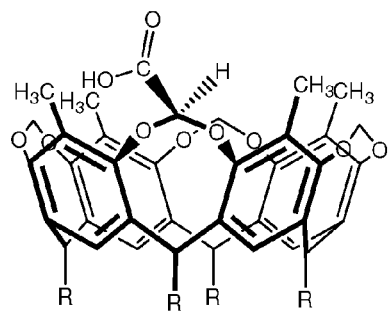
FIG. 2 shows the in and out isomers of the COOH cavitand and the Tiiii and TSiiii cavitands.
Figure 2:
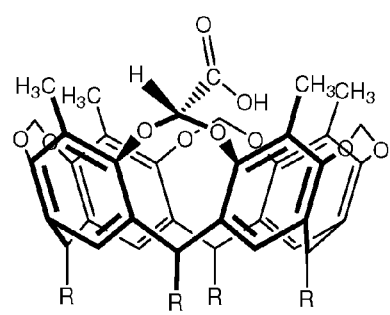
Figure 2:
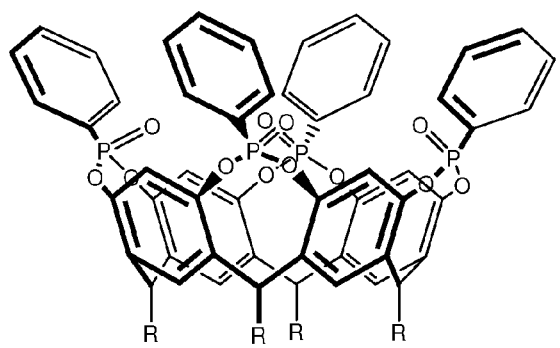
Figure 2:
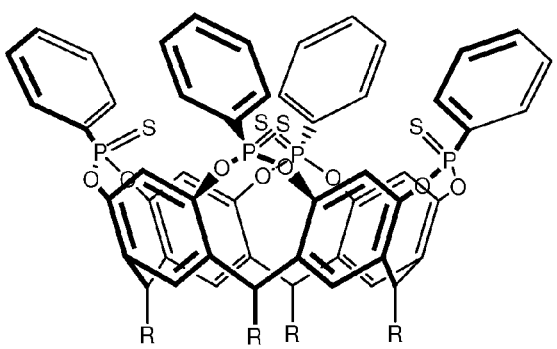
Figure 3:
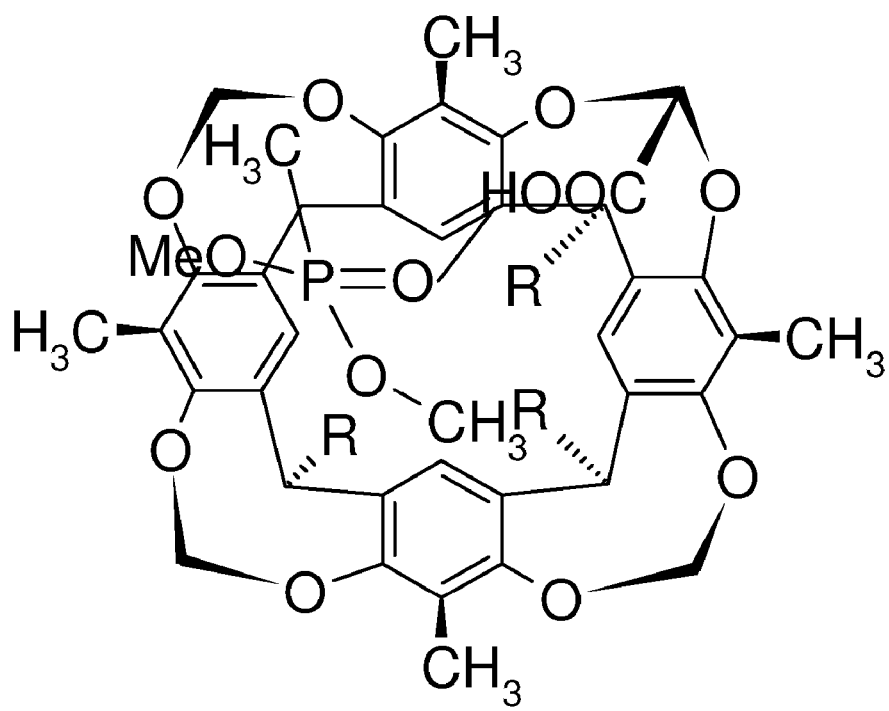
FIG. 3 shows a possible interaction between DMMP and a cavitand having a carboxylic group.

A modification of this compound has four alkyl groups, including but not limited to pentyl and undecyl, on the lower bridging methylene groups. A side view of one example compound is shown in FIG. 1. FIG. 2 shows side views of the in and out isomers of a cavitand. This compound may be used in a device for detecting an analyte by measuring the change in the refractive index of a film of the compound before and after potential exposure to an analyte. The device may include a surface plasmon resonance apparatus and a system capable of correlating a change in the refractive index to the concentration of the analyte. The analyte may be a nerve agent, including but not limited to DMMP. FIG. 3 shows a possible interaction between DMMP and a cavitand having a carboxylic group. The methyl groups ($R^1$) on top of the cavity may serve two purposes: increasing the depth of the cavity and strengthening the CH-π interactions. Both isomers may have the same response in a detector.

In another embodiment, the cavitand contains bridging phosphorus atoms instead of methyl groups between the oxygen atoms, as shown in FIG. 2. The phosphorus atoms have pendant phenyl groups oriented away from the central cavity and double-bonded oxygen or sulfur atoms oriented towards the cavity. The compound may contain all oxygen (Tiiii [$C_{11}H_{23}$, H, Ph]) or all sulfur (TSiiii[$C_{11}H_{23}$, H, Ph]) atoms bound to the phosphorus.

The design of cavitand receptors for organophosphorus vapors recognition has been based on previous experiences in alcohols (Pinalli et al. *Eur. J. Org. Chem.* 2004, 451-462) and acetates detection (Suman et al. *J. Supramol. Chem.* 2002, 2, 97-106). The design is related to the diagnostic O=P—$OCH_3$ moiety, addressing the "acidic" methyl group via inclusion within a π-basic cavity and the P=O group via H-bonding with a COOH H-bonding donor. The desired cooperativity between the two interactions is obtained introducing the COOH group on one of the bridging groups at the upper rim of the cavity. The four methyl substituents in the apical positions have been added to deepen the cavity and increase its π-basic character. Both factors are relevant to strengthening host-guest CH-π interactions.

The high sensitivity of the optical SPR technique to transduce the interaction of chemical vapors with cavitands has been demonstrated. In addition it has been demonstrated that cavitand selectivity is not affected by the process used for coating cavitands onto surfaces used for SPR experiments. Further, it has been established that cavitands may be deposited in preferred orientations on hydrophobic and hydrophilic surfaces. For example, on a hydrophilic surface the head groups or cavities point onto the surface while if the surface is hydrophobic, the cavities point away from the surface. This phenomenon can allow control over the molecular orientation of the cavitands, which is important for increasing the efficiency of chemical vapor interaction (Lagugne-Labarthet et al. *Chem. Phys. Lett.* 381, 322 (2003)).

Figure 4:
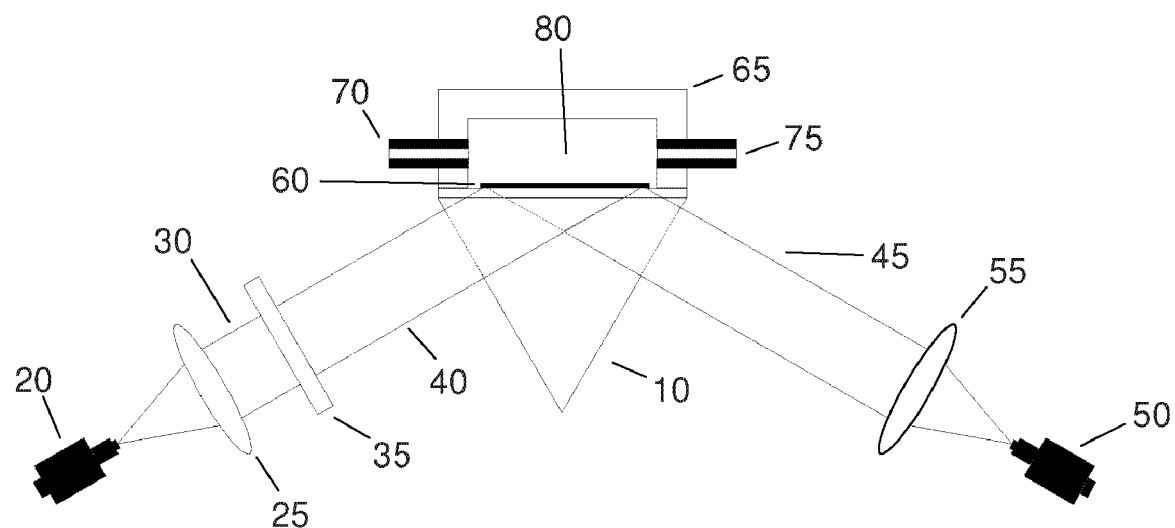
FIG. 4 schematically illustrates an SPR sensing apparatus.
Figure 5:
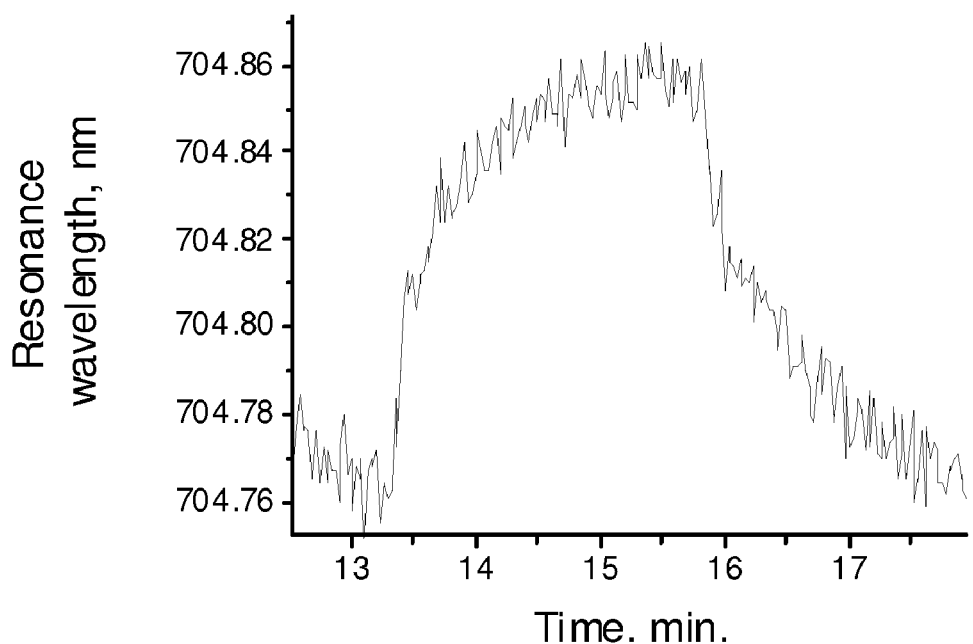
FIG. 5 shows real-time SPR signal obtained with cavitand coating and DMMP vapor exposure at 2 ppb. Note the fast response kinetics as well as the complete recovery of the baseline when the vapors are not exposed.
Figure 6:
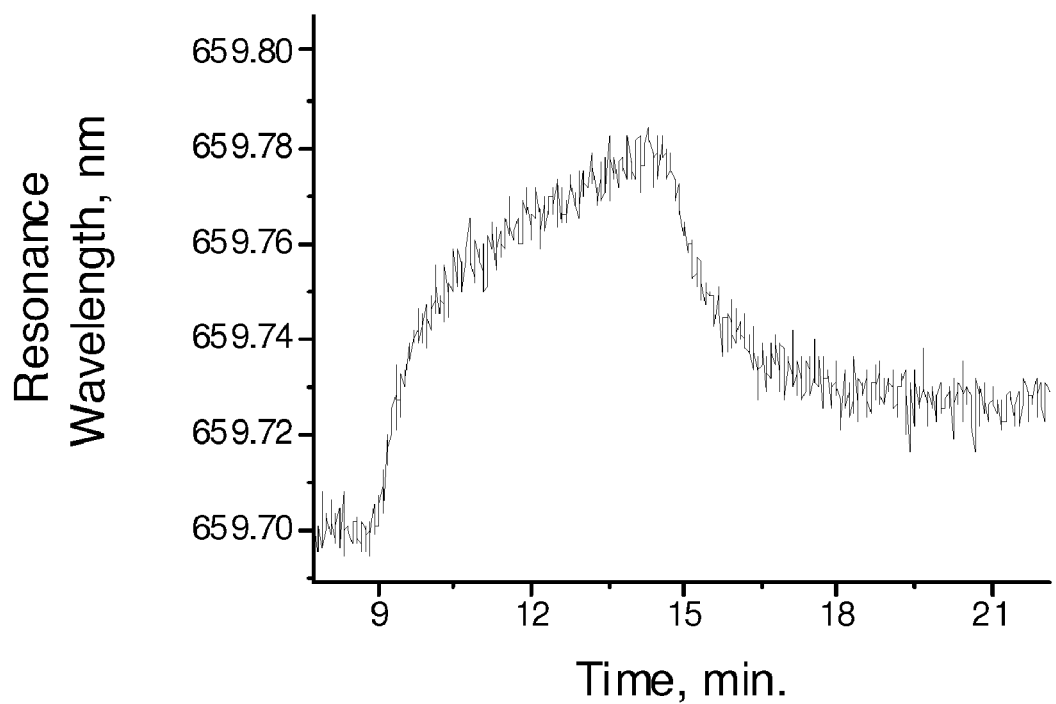
FIG. 6 shows the SPR signal obtained from exposure of polymer FPOL to DMMP vapors at 2 ppb
Figure 7:
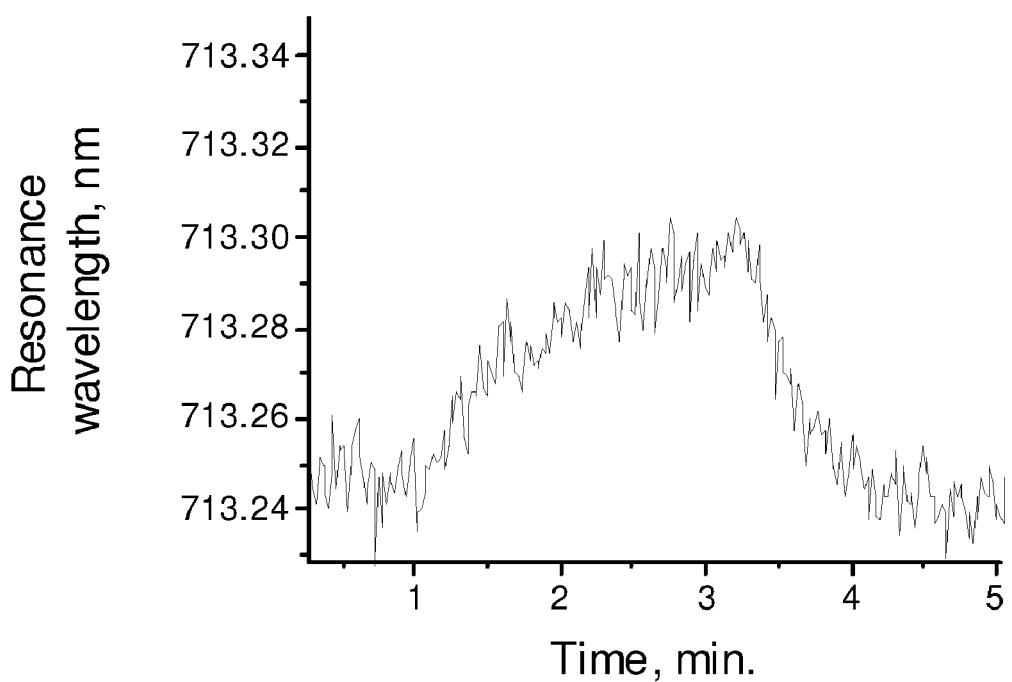
FIG. 7 shows the SPR signal obtained from exposure of coating MHDA to DMMP vapors at 2 ppb
Figure 8:
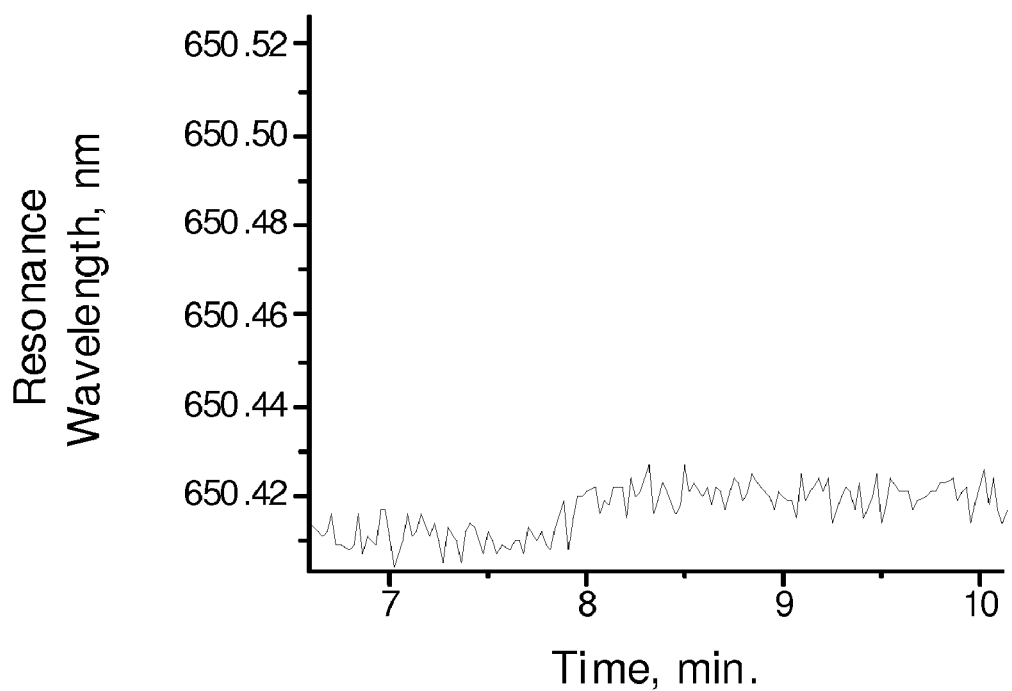
FIG. 8 shows the SPR signal obtained from exposure of PECH polymer layer to DMMP vapors at 2 ppb.

A schematic of an embodiment of the device is shown in FIG. 4, showing prism 10, sensing layer 60, multimode fiber optic 20 placed at the focus of a convex achromatic lens 25 used to generated collimated polychromatic light 30, rotatable polarizer 35 placed after the collimating lens, polarized light 40 directed onto the entrance face of the prism 10, light exiting the opposite face of the prism 45 focused onto another multimode fiber 50 by a second convex achromat 55, flow cell 65 comprising an inlet 70 and outlet 75 for the chemical vapors, and a rectangular aperture 80 for the prism and substrate.

The cavitand may permit highly sensitive and selective chemical vapor detectors that use coating materials to transducer the interaction of vapors with the coating. The selectivity principle is similar to that of natural protein molecules that bind with high specificity due to the presence of binding pockets that have a specific shape, size, and interactions.

Having described the invention, the following examples are given to illustrate specific applications of the invention. These specific examples are not intended to limit the scope of the invention described in this application.

EXAMPLE 1

Comparison of COOH to other sensing layers—For this work four different class of sensing layers were chosen cavitands, polyepichlorohydrin (PECH), fluoropolyol (FPOL), and self assembled monolayer of mercaptohexadecanoic acid (MHDA). Well defined cavitands films were obtained by Langmuir and Blodgett method on gold. Well defined MHDA interfaces were obtained by solution self assembly of long chain ω-substituted thiol molecules, on gold surfaces. PECH (1 mg/mL in chloroform) and FPOL (1 mg/mL in chloroform) were spin coated (4000 rpm for 60 sec) on gold for comparison with the other sensing layers. The molecular recognition properties of PECH, FPOL, and monolayer of thiols with different functional groups have been extensively studied using different transduction schemes and exploited as sensitive layers in chemical sensors. The research presented here demonstrates that methylene-bridged cavitands where one carboxylic acid functional group attached at one side of the upper rim of the cavity without specific orientation (either inward or outward with respect to the cavity) can be used in conjunction with SPR detection as sensing devices for dimethylmethylphosphate (DMMP), a model molecule for the nerve gases such as sarin, in the vapor phase, thereby extending the range of applications for such sensing materials.

The interaction of DMMP with cavitands was analyzed under sensor conditions by a surface plasmon resonance spectroscopy (SPR), sensitive to changes in refractive index. It was found that DMMP interacts with hydrogen bond donating groups (—COOH group on the cavity) and that the lone pair electrons of the P=O oxygen is the main interacting part of the molecule.

Experimental process for coatings—The procedure used for preparation of monolayer, MHDA was as follows: To obtain a monolayer, the gold-coated substrate was immersed into 1 mM solution of the adsorbate in a mixture of ethanol: chloroform (7:3, v/v). Substrates were left in the $C_{18}$ thiol solution for six hours for self-assembly of monolayers on the gold surface.

To coat the polymer layers, PECH and FPOL, the following procedure was used: A cover glass was cleaned prior to gold deposition with a hot "piranha" solution (30:70 v/v mixture of $H_2O_2$ and $H_2SO_4$). The gold metal film, required by SPR for generating plasmons was deposited onto the cleaned cover glass (22mm×22mm, THOMAS SCIENTIFIC) using a vacuum evaporator (Edwards Auto 306). Evaporation, from a gold coin (Canadian coin, 99.99%), was preformed at a vacuum of $10^{-6}$ bar and at a rate of 0.02-0.04 nm/s resulting in a 50 nm gold film on the cover glass, as determined via a crystal oscillator. The sensing layer was produced by spin coating (Model P6700) a solution of cavitand 1 or 2 (0.38 mM in acetone) at 4000 rpm for 60 s at room temperature. Polyepichlorohydrin (PECH) solution (0.1% in chloroform) was spin coated (4000 rpm for 60 s) on gold as a reference sensing layer. Preparation of thin layer of cavitands was performed using Langmuir and Blodgett method.

Results—The change in resonance wavelength as a function of time for 2 ppb DMMP in contact with the cavitands, MHDA, PECH, and FPOL is plotted in FIGS. 5, 6, 7, and 8 respectively. Langmuir-type isotherms are observed for all sensing layer with DMMP. The interaction between these cavitands and FPOL towards 2 ppb DMMP gives comparable resonance wavelength shift response compared to the other MHDA and PECH. The resonance wavelength shift increase due to cavitands FPOL, and MHDA resulted from H-bonding interactions with DMMP. In the case of PECH the resonance wavelength shift is close to the noise level of the instruments and not detectable due to low interaction with DMMP.

Figure 9:
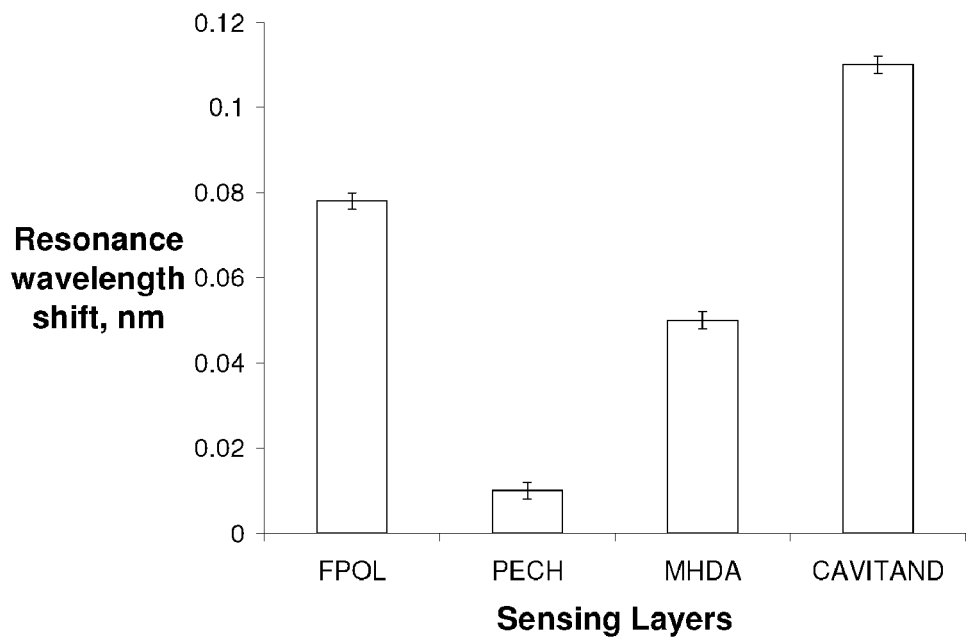
FIG. 9 shows SPR wavelength shift due to the interaction of 2 ppb of DMMP with four different sensing layers.

To get an overview of the response of all the four sensing systems towards 2 ppb DMMP analytes, bar graphs were generated (FIG. 9). The bar graph illustrates the relative change in resonance wavelength shift at equal concentration (2 ppb) of the analyte vapors. The Y-axis represents the change in resonance wavelength shift due to sensing layer-DMMP interaction.

The high sensitivity of cavitands and, to a minor extent of FPOL toward DMMP is clearly shown in FIG. 9. Close comparison of cavitand with FPOL, self-assembled MHDA, and PECH illustrates the effect of synergistic CH-$\pi$ and H-bonding interactions on DMMP uptake by the cavitand.

The complete reversibility of the response has also been verified using cavitands compared to FPOL. For this, the guest host complex was exposed to a steady stream of nitrogen gas which effectively dislodged DMMP from the sensing layer as evidenced by the reversal of the resonance wavelength (see FIGS. 5, 6, 7, and 8 for reversibility of sensing layer). This is understandable because the guest host interactions are inherently non covalent in nature and therefore reversible. The potential for use of these cavitands on an SPR sensing platform with recycling capability has thus been clearly demonstrated.

EXAMPLE 2

Synthesis of COOH, Tiiii[$C_{11}H_{23}$, H, Ph], and TSiiii [$C_{11}H_{23}$, H, Ph]—The synthesis is outlined in Scheme 1 below: partial bridging of pentyl-footed resorcinarene 1 was obtained by operating in defect of bromochloromethane. The desired carboxylic acid was then introduced on the remaining pair of phenolic OHs in the form of ester using methyl dichloroacetate as bridging reagent to give cavitands 3-out and 4-in in 44% and 34% isolated yields respectively, after column chromatography separation. Hydrolysis of both cavitands with potassium carbonate in ethanol/water led to the corresponding carboxylic acid derivatives COOH-out and COOH-in.

All reactions were conducted under an argon atmosphere. NMR spectra were recorded on a Brucker Avance spectrometer. $^1$H NMR were recorded at 300 and 400 MHz and all chemical shifts ($\delta$) were reported in ppm relative to the proton resonance resulting from incomplete deuteration of the NMR solvent: CDCl$_3$ (7.24 ppm). MALDI-TOF mass spectra were obtained on a PerSpective Biosystem Voyager DE-RP spectrometer equipped with delayed extraction, using dithranol as matrix. ESI-MS experiments were performed on a Waters ZMD spectrometer equipped with an electrospray interface. Microanalyses were performed by the service of Parma University. Thin-layer chromatography (TLC) was performed on commercially prepared silica gel 60F$_{254}$ plates, and column chromatography was performed using Merck 230-400 mesh silica gel 60.

Resorcinarene 1, cavitand Tiiii[$C_{11}H_{23}$, H, Ph] and TSiiii [$C_{11}H_{23}$, H, Ph] were prepared following published procedures (Tunstad et al. *J. Org. Chem.* 1989, 54, 1305-1312; Delangle et al. *Eur. J. Org. Chem.* 2001, 3695-3704; Bibal et al. *Tetrahedron* 2003, 59, 5849-5854). Water vapor was produced from deionized water further purified by a Millipore system.

Trimethylene-bridged resorcinarene (2)—To a stirred solution of resorcinarene 1 (3.00 g, 3.63 mmol) (see Scheme 1 below) in dry DMF (20 mL), bromochloromethane (0.56 mL, 8.70 mmol) and potassium carbonate (3.01 g, 21.8 mmol) were added at once. The reaction mixture was stirred for four hours at 90° C. and then quenched in acidic water. The resulting precipitate obtained was filtered and dissolved in dichloromethane: the organic solution was washed to neutrality and then the solvent was removed in vacuo.

Purification by column chromatography on silica gel with eluant 8:2 hexane:acetone afforded compound 2 (yield 24%) and the corresponding tetrabridged cavitand (yield 11%) as white solids.

The configuration of in/out isomers was assigned on the basis of the different chemical shifts of the protons on the carbomethoxy group and of the corresponding hydrogen on the same bridge, according to their orientation inward or outward with respect to the cavity. Protons inside the cavity resonate at higher field with respect to their outside counterparts, a feature diagnostic of inward orientation.

$^1$H NMR (CDCl$_3$, 300 MHz) $\delta$ 0.89 (m, 12H, CH$_3$), 1.35 (m, 24H, —(CH$_2$)$_3$—), 2.02 (s, 6H, ArCH$_3$), 2.17 (s, 6H, ArCH$_3$), 2.21 (m, 8H, CH—CH$_2$), 4.21 (d, 1H, O—CH$_{in}$—O, $^2$J=7.0 Hz), 4.31 (d, 2H, O—CH$_{in}$—O, $^2$J=7.0 Hz), 4.34 (t, 1H, CH, $^3$J=8.0 Hz), 4.71 (t, 1H, CH, $^3$J=8.2 Hz), 4.77 (t, 2H, CH, $^3$J=8.1 Hz), 5.83 (d, 1H, O—CH$_{out}$—O, $^2$J=6.9 Hz), 5.88 (d, 2H, O—CH$_{out}$—O, $^2$J=7.0 Hz), 6.40 (bs, 2H, OH), 7.00 (s, 2H, ArH), 7.03 (s, 2H, ArH). MALDI-TOF MS (m/z) (%) 861.3 [M$^+$, (100)], [M=C$_{55}$H$_{72}$O$_8$].

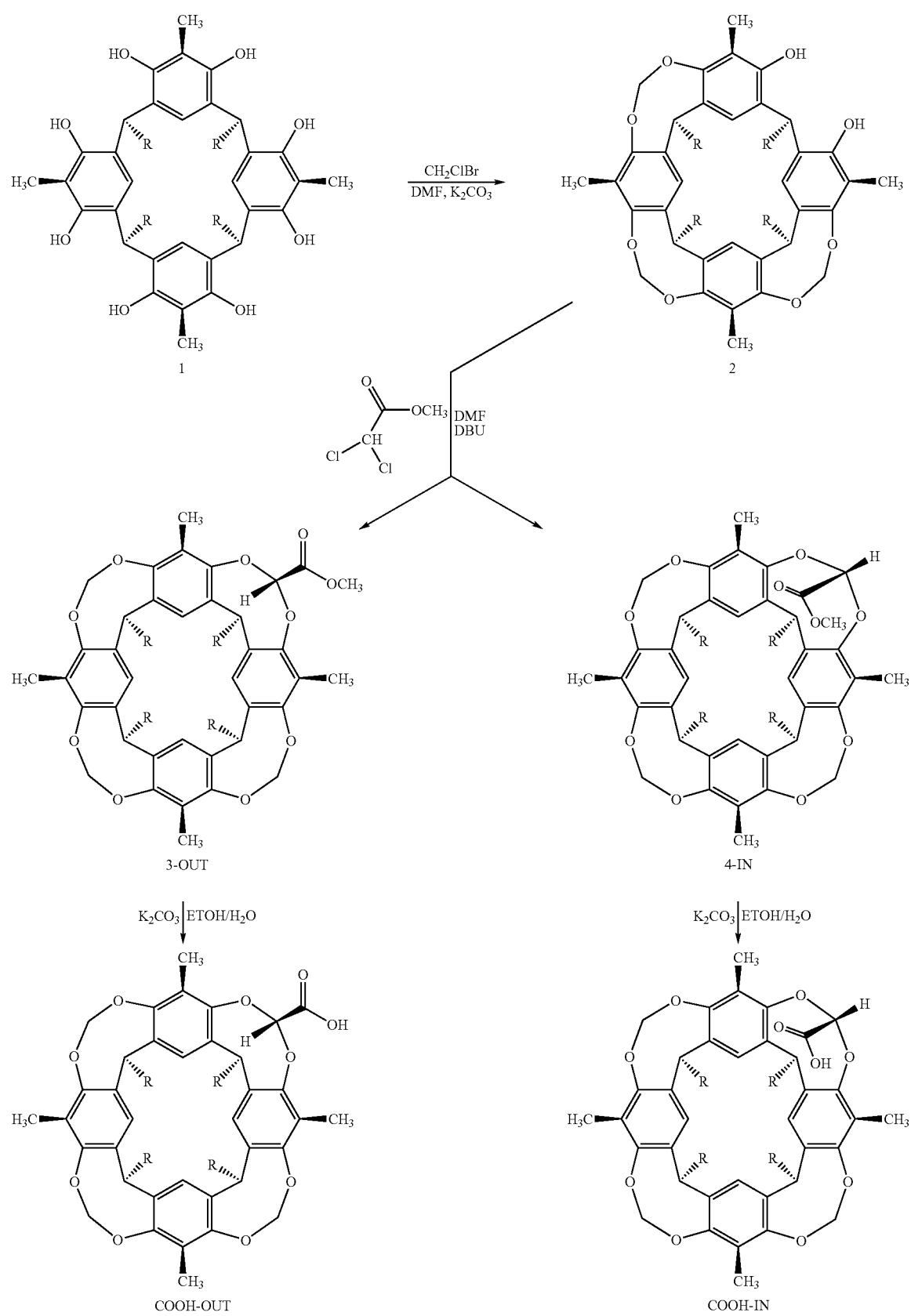

Upper rim COOCH$_3$ cavitands (3) (out isomer) and (4) (in isomer)—To a stirred solution of tri-bridged resorcinarene 2 (0.75 g, 0.87 mmol) and methyl dichloroacetate (0.36 mL, 3.48 mmol) in dry DMF (50 mL), DBU (261 μL, 2.61 mmol) was added dropwise. The mixture was heated at 80° C. for 6 hours and then quenched in acidic water. The precipitate obtained was filtered and washed to neutrality. Purification by column chromatography on silica gel with eluant 9:1 methylene chloride:cyclohexane afforded 3-out (yield 44%) and 4-in (yield 34%) as white solids.

3-out: TLC R$_f$=0.4. $^1$H NMR (CDCl$_3$, 300 MHz) δ 0.88 (t, 12H, CH$_3$), 1.35 (m, 24H, —(CH$_2$)$_3$—), 1.97 (s, 6H, ArCH$_3$), 1.99 (s, 6H, ArCH$_3$), 2.16 (m, 8H, —CH—CH$_2$), 3.96 (s, 3H, COOCH$_3$ out), 4.23 (d, 2H, O—CH$_{in}$—O, $^2$J=6.9 Hz), 4.24 (d, 1H, O—CH$_{in}$—O, $^2$J=6.9 Hz), 4.66 (s, 1H, CH$_{in}$—COOCH$_3$), 4.75 (m, 4H, CH), 5.88 (d, 1H, O—CH$_{out}$—O, $^2$J=6.9 Hz), 5.89 (d, 2H, O—CH$_{out}$—O, $^2$J=6.9 Hz), 6.97 (s, 2H, ArH), 6.99 (s, 2H, ArH). MALDI-TOF MS (m/z) (%) 930.8 [M$^+$, (100)], 953.7 [(M+Na)$^+$, (80)], [M=C$_{58}$H$_{74}$O$_{10}$].

4-in: TLC R$_f$=0.2. $^1$H NMR (CDCl$_3$, 300 MHz) δ 0.90 (m, 12H, CH$_3$), 1.37 (m, 24H, —(CH$_2$)$_3$—), 1.81 (s, 6H, ArCH$_3$), 1.99 (s, 6H, ArCH$_3$), 2.16 (m, 8H, —CH—CH$_2$), 3.29 (s, 3H, COOCH$_3$ in), 4.16 (d, 2H, O—CH$_{in}$—O, $^2$J=6.9 Hz), 4.46 (d, 1H, O—CH$_{in}$—O, $^2$J=7.0 Hz), 4.60 (t, 1H, CH, $^3$J=7.9 Hz), 4.70 (t, 2H, CH, $^3$J=8.3 Hz), 4.78 (t, 1H, CH, $^3$J=7.9 Hz), 5.80 (d, 2H, O—CH$_{out}$—O, $^2$J=6.9 Hz), 5.88 (d, 1H, O—CH$_{out}$—O, $^2$J=7.0 Hz), 6.18 (s, 1H, CH$_{out}$—COOCH$_3$), 6.98 (s, 2H, ArH), 7.26 (s, 2H, ArH). MALDI-TOF MS (m/z) (%) 931.6 [M$^+$, (70)], 953.8 [(M+Na)$^+$, (100)], [M=C$_{58}$H$_{74}$O$_{10}$].

Upper rim COOH cavitands (5) (out isomer) and (6) (in isomer)—To a stirred solution of 3-out or 4-in (0.275 g, 0.29 mmol) in 30 mL of 95% ethanol a solution of potassium carbonate (0.400 g, 0.83 mmol) dissolved in 3 mL of water was added. The resulting suspension was heated for 3 hours at 78° C., until a clear solution was formed. Removal of the solvent followed by addition of acidic water (pH=2) led to a precipitate, which was purified by column chromatography using 19:1 dichloromethane:ethanol as eluant. Cavitand COOH-out (yield 70%) and COOH-in (yield 74%) were obtained in pure form as white solids.

COOH-out: $^1$H NMR (CDCl$_3$, 300 MHz) δ 0.91 (t, 12H, CH$_3$), 1.39 (m, 24H, —(CH$_2$)$_3$—), 1.97 (s, 6H, ArCH$_3$), 2.02 (s, 6H, ArCH$_3$), 2.19 (m, 8H, —CH—CH$_2$), 4.24 (m, 3H, O—CH$_{in}$—O), 4.71 (s, 1H, CH$_{in}$—COOH), 4.75 (m, 4H, CH), 5.89 (m, 3H, O—CH$_{out}$—O), 6.97 (s, 2H, ArH), 6.99 (s, 2H, ArH). ESI-MS (m/z)(%) 939.9 [(M+Na)$^+$, (100)], 955.5 [(M+K)$^+$, (50)] [M=C$_{57}$H$_{72}$O$_{10}$]. Anal. Calcd. for C$_{57}$H$_{72}$O$_{10}$: C, 74.64; H, 7.91. Found: C, 74.45; H, 8.03.

COOH-in: $^1$H NMR (CDCl$_3$, 300 MHz) δ 0.90 (m, 12H, CH$_3$), 1.37 (m, 24H, —(CH$_2$)$_3$—), 1.76 (s, 6H, ArCH$_3$), 1.98 (s, 6H, ArCH$_3$), 2.18 (m, 8H, —CH—CH$_2$), 3.95 (d, 2H, O—CH$_{in}$—O, $^2$J=6.6 Hz), 4.32 (d, 1H, O—CH$_{in}$—O, $^2$J=7.1 Hz), 4.57 (t, 1H, CH, $^3$J=7.9 Hz), 4.69 (t, 2H, CH, $^3$J=8.3 Hz), 4.80 (t, 1H, CH, $^3$J=7.9 Hz), 5.78 (d, 2H, O—CH$_{out}$—O, $^2$J=6.6 Hz), 5.92 (d, 1H, O—CH$_{out}$—O, $^2$J=7.1 Hz), 6.01 (s, 1H, CH$_{out}$—COOH), 6.96 (s, 2H, ArH), 6.98 (s, 2H, ArH). ESI-MS (m/z) (%) 939.9 [(M+Na)$^+$, (100)], 955.9 [(M+K)$^+$, (50)] [M=C$_{57}$H$_{72}$O$_{10}$]. Anal. Calcd. for C$_{57}$H$_{72}$O$_{10}$: C, 74.64; H, 7.91. Found: C, 74.39; H, 8.10.

EXAMPLE 3

Sensing layer preparation—A glass slide was cleaned prior to gold deposition with hot "piranha" solution (30:70 v/v mixture of H$_2$O$_2$ and H$_2$SO$_4$). (Solution reacts violently with many organic materials and must be used with extreme caution and should not be stored in sealed containers). An approximately 2 nm thick chromium adhesion layer was first deposited onto the cleaned slide using a vacuum evaporator (Edwards Auto 306). This was followed by evaporation of a nearly 50 nm thick gold layer for SPR. Evaporation, from a gold coin (Canadian coin, 99.99%), was preformed at a vacuum of 10$^{-6}$ bar and at a rate of 0.02-0.04 nm s$^{-1}$ with the thickness of the deposited metal films determined via a crystal oscillator.

Two different types of sensing layers were coated onto the gold surfaces: cavitands and fluoropolyol (FPOL). Four different cavitands were used in this work denoted COOH-out, COOH-in, Tiiii[C$_{11}$H$_{23}$, H, Ph] and TSiiii[C$_{11}$H$_{23}$, H, Ph]. Each of these cavitands has four alkyl feet that are either 5 or 11 carbons in length. The cavities of these cavitands are identical except for functionalization at the upper rim. COOH-out and COOH-in each contain one carboxylic group at the upper rim either pointing out of or into the cavity, respectively. Tiiii[C$_{11}$H$_{23}$, H, Ph] has four P=O groups pointing into the cavity, while TSiiii[C$_{11}$H$_{23}$, H, Ph] has four P=S groups pointing into the cavity. The cavitand and polymer sensing layers were produced by spin coating (Model P6700) a solution of cavitand or fluoropolyol (0.5 mM in acetone) at 2000 rpm for 60 s at room temperature onto a gold coated substrate. Hassan and co-workers showed that the thickness of spin-cast cavitand layers is consistent with hydrodynamic theory for spinning of a low-viscosity and highly volatile liquid (Hassan et al. *IEE Proc.-Sci. Meas. Technol.* 2000, 147, 137-140). COOH cavitands were also deposited onto gold surfaces via Langmuir-Blodgettry. Two, four or eight layers of cavitand were deposited onto the hydrophobic gold surface to produce cavitand layers with head groups facing away from the gold surface. The film pressure was fixed at 35 mN/m during the deposition.

Ellipsometry profiles of each bare gold surface and sensing layer were measured with a model EC110 multi-wavelength ellipsometer (J.A. Woollam Co. Inc) equipped with a model LPS-300 75 W Xenon light source at an incident angle of 70°. The ellipsometry curves were fit to a 2 layer model (a gold layer and a Cauchy layer) to calculate the thickness of each sensing layer using WVASE 32 Version 3.337b software.

EXAMPLE 4

SPR measurements—A variable wavelength surface plasmon resonance (SPR) experimental arrangement, based on the Kretschmann configuration (Kretschmann et al. Teil A 1968, 23, 2135-2136) was used for all the measurements. A 17 mm high×22 mm×32 mm, BK7 glass prism (Howard Johnson Optical Laboratories) was index matched to the gold coated substrate with an index matching liquid (Cargille Inc.). A 5 V halogen bulb (Ocean Optics) provided a polychromatic light source for the variable wavelength SPR. A 20 mm lens (Edmonds Optics) was used to collimate the divergent white light. A polarizer was placed in the path of the beam to ensure that p-polarized light was incident on the glass prism. The reflected light was collected and monitored using a CCD spectrometer (Ocean Optics). Each CCD represents a pixel that integrates the number of impinging photons to determine its intensity. The pixel data was converted to wavelength using a calibration procedure. The angle of incidence was fixed at 37.5 degrees for all experiments.

To expose organic vapors of precisely known concentration to cavitands, a flow cell was constructed from a block of Teflon. An o-ring ensured a good seal between the prism/slide and Teflon chamber. To generate parts per billion to parts per million organic vapor concentrations, a diffusion vial with a 5.0 mm diameter capillary (VICI Metronics) was filled with analyte liquid using 5 ml syringe needles (VICI Metronics) and placed in one side of a U-tube. Glass beads where placed on the other side. The U-tube was placed in a temperature controlled (to within 0.1 degrees) water bath (PolySciences Inc). Vapors of the organic liquid were diluted with a stream of nitrogen carrier gas. The flow of both the carrier gas and the analyte were precisely controlled (accuracy of 1-2%) using DFC mass flow controllers (AALBORG INC.) and mixed in the appropriate proportions before being introduced into the flow cell for exposure to the cavitands. An SPR baseline was collected for each sensing layer during exposure to flowing nitrogen. After sufficient baseline collection, the analyte vapor was introduced into the flow chamber at a specified concentration. Care was taken to ensure that analyte was introduced into the SPR flow cell after the diffusion vial came to equilibrium with respect to vapor concentration. A software program controlled the flow of the carrier gas and the organic vapors.

Figure 10:
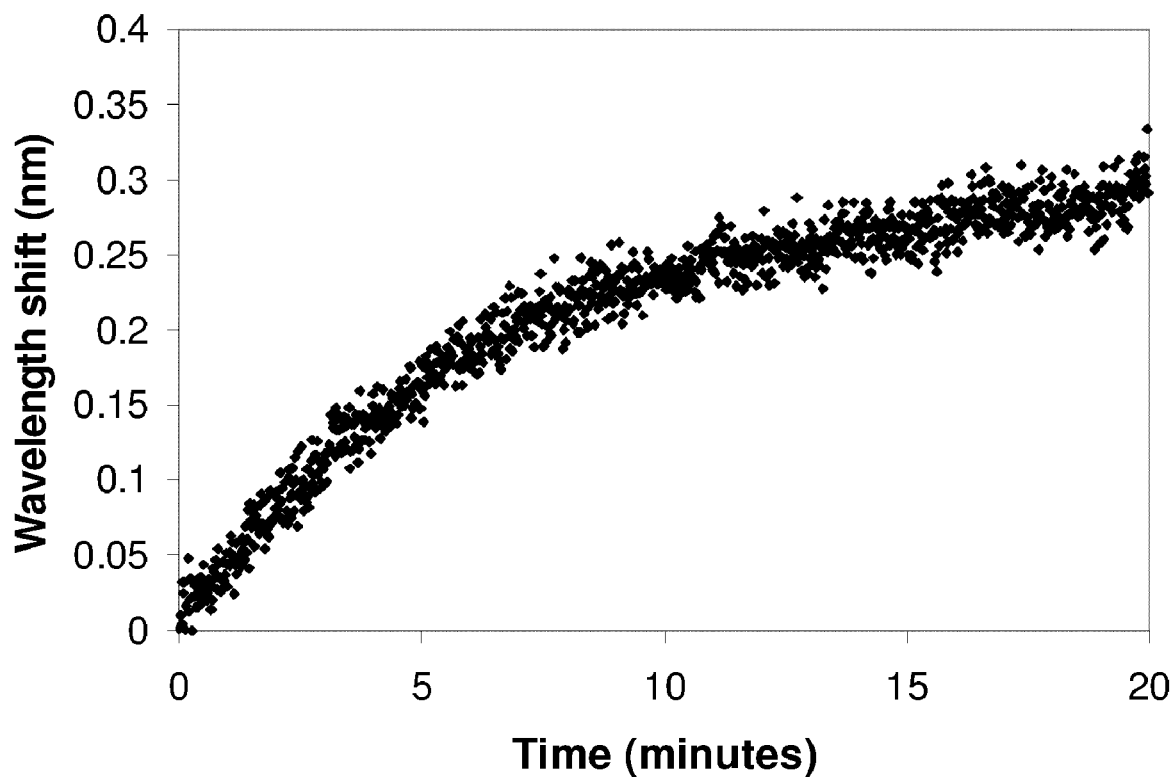
FIG. 10 shows the SPR wavelength shift upon exposure of a spin-cast layer of COOH-out to a 4.475 ppm concentration of DMMP.

DMMP adsorption to COOH cavitand layers—The association of DMMP with cavitand at the interface was monitored by measuring the change in SPR wavelength ($\Delta\lambda$) as the analyte containing vapor entered the gas flow chamber. Typical kinetics of the SPR wavelength shift upon exposure of a spin-cast film of COOH-out to 4.475 ppm DMMP are shown in FIG. 10. The SPR shift increases rapidly initially indicating reasonable quick association with the cavitand surface. The SPR wavelength shift reached a pseudo-plateau after approximately 4-7 minutes, and continued to increase at a slower rate. The SPR signal shift to noise ratio of approximately 10 is very good at this DMMP concentration.

Figure 11:
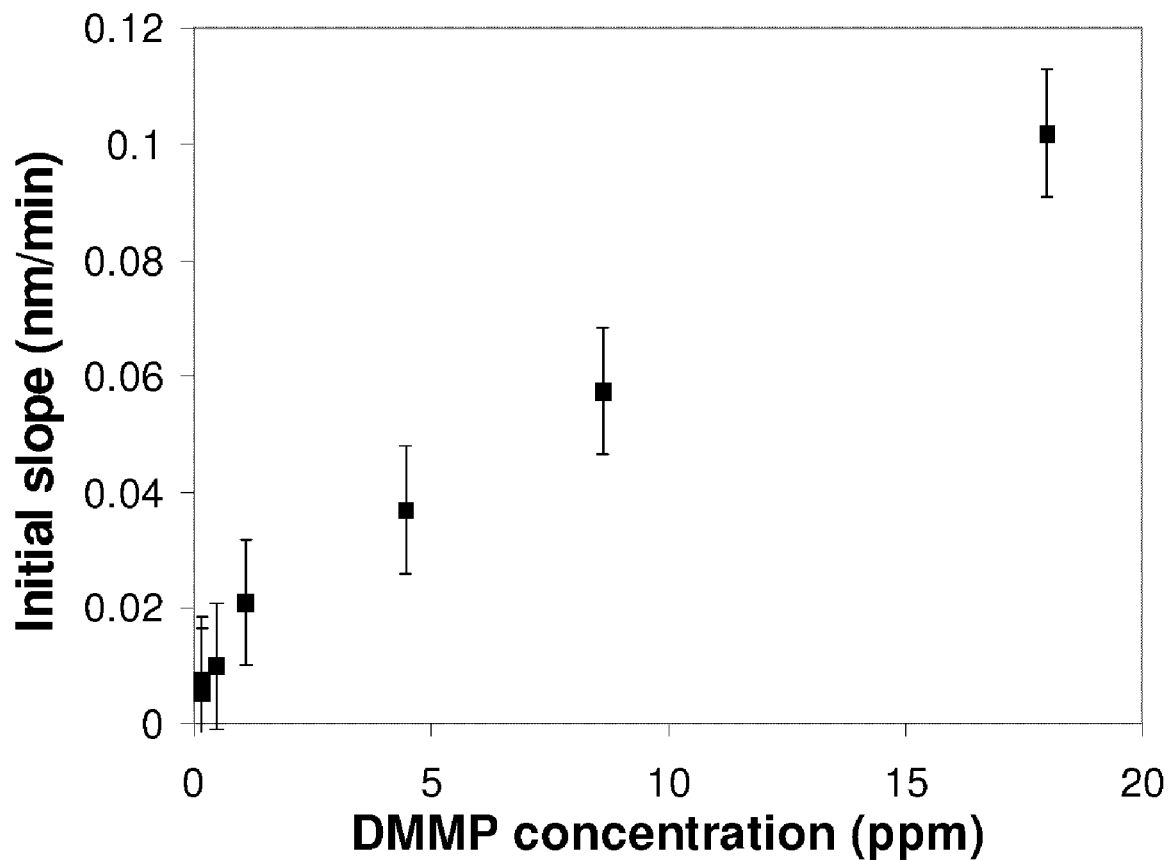
FIG. 11 shows the initial rate of SPR signal shift upon interaction of DMMP with COOH-out.
Figure 12:
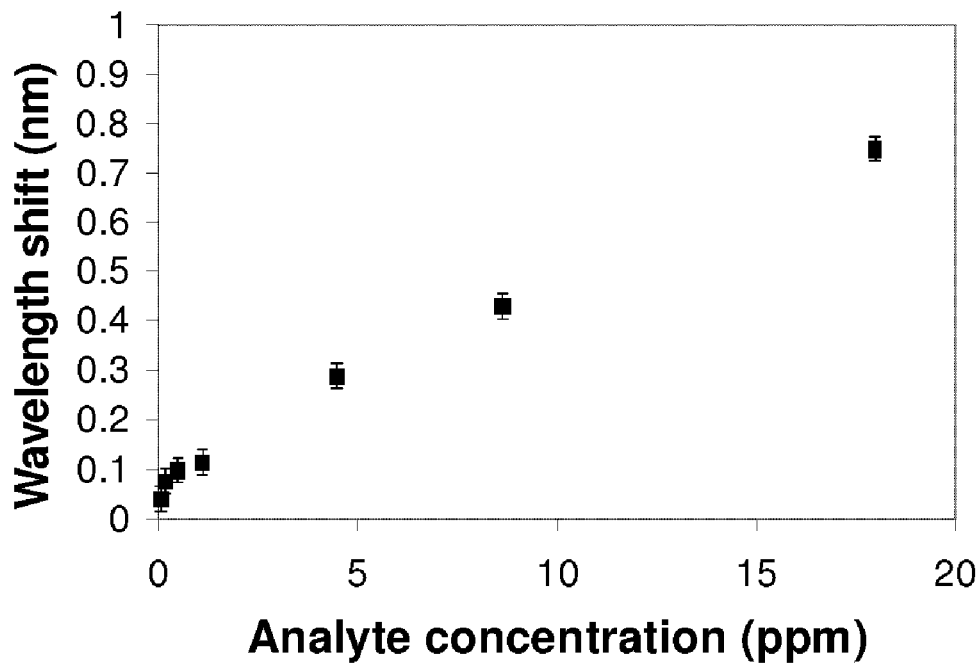
FIG. 12 shows the extent of SPR signal shift after 20 minutes of DMMP exposure to COOH-out as functions of the DMMP concentration.

Both the rate and total shift of the SPR wavelength during DMMP exposure to the spin-cast COOH-out vary with concentration. FIG. 11 shows the initial rate of the SPR wavelength shift at different DMMP concentrations. The rate of SPR response to DMMP increased with concentration. The total wavelength shift after the COOH-out surface was exposed to 20 minutes of different DMMP concentrations is shown in FIG. 12. After this 20 minute time period, the SPR signal shift reached a pseudo-plateau but continued to increase more slowly. This total wavelength shift after 20 minutes also increased with DMMP concentration. Hence, a sensor using this technology would respond more rapidly to higher concentrations of DMMP. It is important to note that although it takes 4-7 minutes for DMMP adsorption to the spin-cast COOH-out layer to reach the pseudo-plateau, the initial change in signal is large, and a response to DMMP binding, beyond the noise of the instrument, can be detected much more quickly, depending on the DMMP concentration. For a DMMP concentration of 4.475 ppm, the SPR wavelength shift exceeds the noise in less than a minute.

Figure 13:
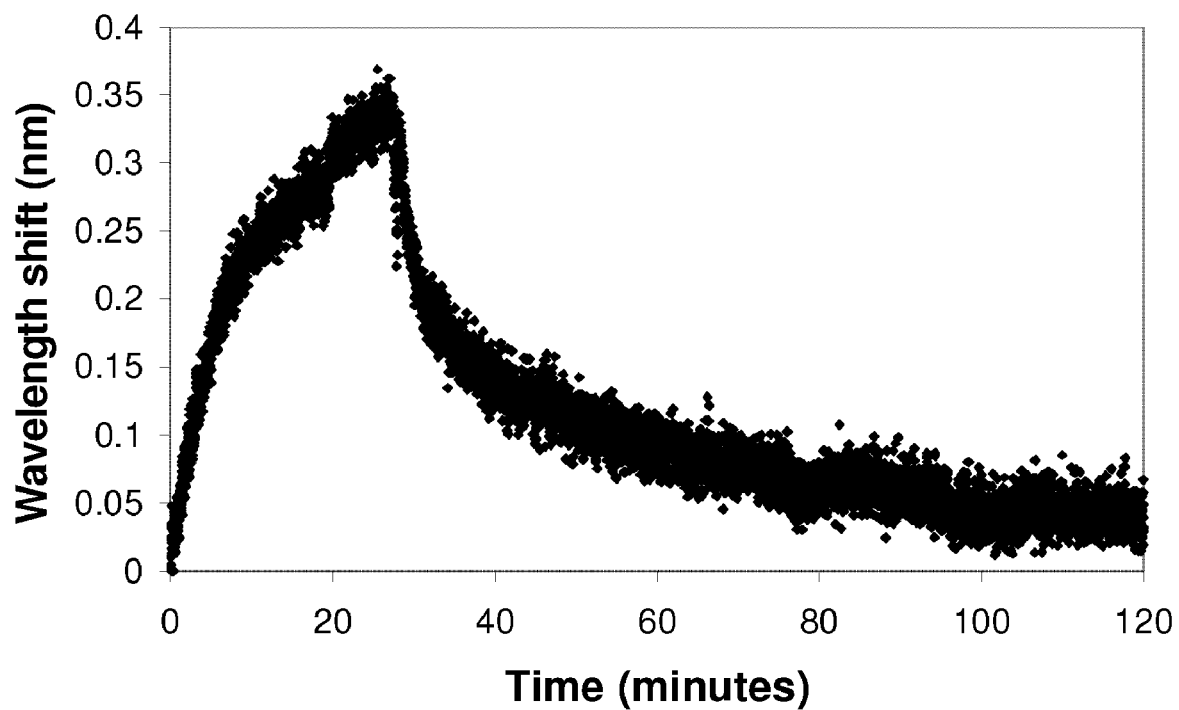
FIG. 13 shows the reversibility of the SPR signal shift when the analyte is removed from the flow line following 25 minutes of DMMP exposure to the spin-cast COOH-out surface.

It is preferable that gas sensors be reusable, which requires that adsorption of analyte be reversible. FIG. 13 shows the sorption and reversibility behavior of DMMP on the COOH-out surface. In most experiments, the SPR signal returned to the original baseline indicating good reversibility of DMMP adsorption to the COOH-out surface. Some reversibility experiments show some hysteresis due to baseline drift, particularly after long times of sorption.

Figure 14:
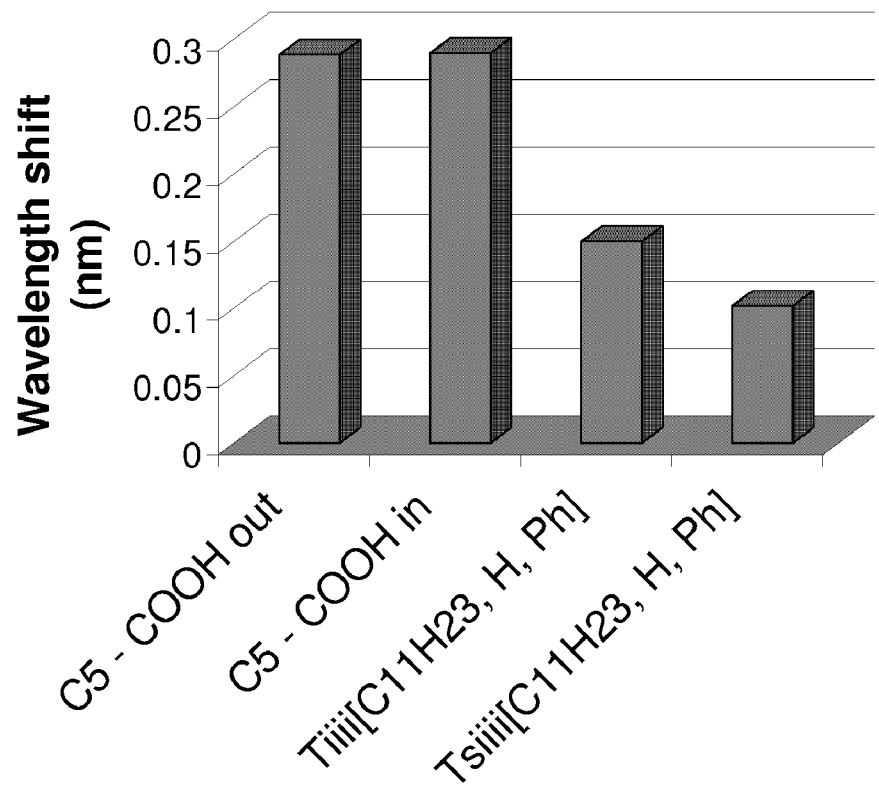
FIG. 14 shows a bar graph showing the extent of SPR wavelength shift after 20 minutes of DMMP exposure to different cavitand surfaces.

Cavitand specificity—The cavitand head group design can be tailored such that a given cavitand interacts preferentially with a certain type of molecule based on size, shape, and specific interactions. The chemical composition of the cavitand head group was systematically varied to evaluate the specificity of the COOH cavitand for DMMP-type molecules. The bar graph in FIG. 14 shows the extent of SPR wavelength shift for different cavitand coatings after 20 minutes of DMMP exposure. All coatings were of similar thickness.

The cavitand head group is known to provide analyte specificity via specific chemical interactions, such as hydrogen bonding or CH-$\pi$ interactions, and steric effects due size and shape complementarity. Hence, the orientation of the identical chemical groups in the cavity might affect the ability of the cavitand to bind a given analyte. The orientation of a P=O group at the rim of a rigid cavity can affect the extent of alcohol detection by the cavitand. QCM measurements showed that cavitands containing a P=O group pointing out of the cavitand did not bind as much alcohol analyte as cavitands with the P=O group pointing into the cavitand (Pinalli et al. *Angew Chem. Int Ed.* 1999, 38, 2377-2380). It was proposed that in order for analyte to interact with the POout cavitand, it had to accomplish the energetically demanding task of carving out a space in the cavitand layer. Hence, alcohols could interact much more easily with cavitands layers that allowed the alcohol to sit in the cavity and simultaneously form a hydrogen bond with the P=O group (Paolesse et al. *Chem. Eur. J* 2003, 9, 5388-5395).

The interaction of DMMP with COOH-in and COOH-out is identical as shown in FIG. 14. This is in agreement with both crystal structure analysis of DMMP.COOH-in complex and molecular modeling prediction of DMMP.COOH-out complex geometry, proving that the orientation of the COOH group is not crucial for this particular analyte.

DMMP interaction with cavitands lacking the COOH group and containing either a hydrogen bond accepting P=O group (Tiiii[$C_{11}H_{23}$, H, Ph]) or a non-hydrogen bonding P=S group (TSiiii[$C_{11}H_{23}$, H, Ph]) in its place was also measured. The interaction of DMMP with these cavitands lacking the COOH group is less than that with COOH containing cavitands even if they present a cavity capable of CH-$\pi$ interactions with methyl groups (Pinalli et al. *Eur. J. Org. Chem.* 2004, 451-462). Hence, the hydrogen bond donating COOH group is significant for cavitand interaction with DMMP.

Contamination of gas sensors is a major limitation in the development of new sensors. The COOH cavitand interaction with ethanol vapor was negligible below an ethanol concentration of 330 ppm. This alcohol concentration is several orders of magnitude higher than the detection limit of DMMP. Furthermore, the interaction of the COOH cavitand with ethanol is much smaller than the interaction of ethanol with the P=O containing Tiiii[$C_{11}H_{23}$, H, Ph], specifically designed for alcohol detection. Hence, it is feasible to construct an array of different cavitands to identify and ratio out alcohol contamination entirely.

Figure 15:
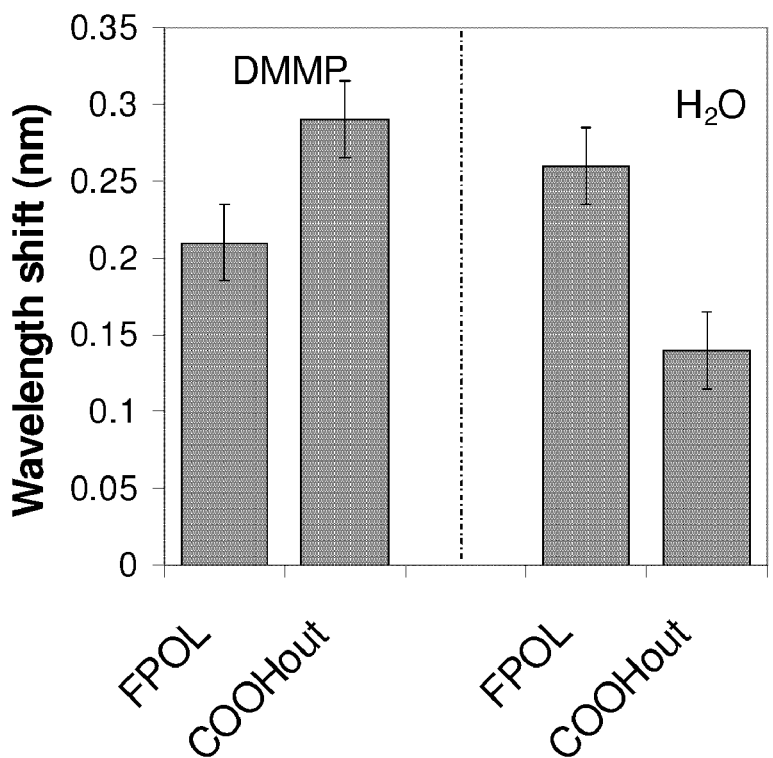
FIG. 15 shows a bar graph showing the extent of SPR wavelength shift after 20 minutes of either DMMP (4.475 ppm) or water vapor (4,193 ppm) exposure to either COOH-out or FPOL.

Vapor interaction with COOH cavitands vs. standard fluoropolyol sensing layers—Fluoropolyol is a common polymeric sensing layer to detect nerve gas agents or simulants, like DMMP. Fluoropolyol coatings are typically coupled with surface acoustic wave (SAW) transduction schemes for DMMP detection. Although the fluoropolyol layer produces a strong SAW response to DMMP, the coating is not specific for DMMP and contamination of the fluoropolyol sensor with water vapor is a major limitation to the practical use of this sensing layer (Rebiere et al. *Sensors and Actuators B* 1997, B 43, 34-39). The bar graph in FIG. 15 shows the extent of SPR wavelength shift of fluoropolyol vs. COOH-out cavitand upon exposure to DMMP or water vapor. The SPR response of a fluoropolyol sensing layer to DMMP was less than that of the COOH-containing cavitand layers. This may be either due to less DMMP adsorption to fluoropolyol than the COOH cavitand layer or to a smaller refractive index change in the sensing layer upon analyte accumulation. It is possible that binding of DMMP to the highly organized cavitand layer triggers a net change in the refractive index of the cavitand layer, which does not occur upon accumulation of DMMP in a fluoropolyol layer.

On the contrary, fluoropolyol interacts more strongly with water vapor than does the COOH cavitand. Hence, the cavitand is less subject to water vapor contamination than is the standard fluoropolyol layer. While the response of the COOH cavitand to DMMP is only slightly better than fluoropolyol, the improved specificity of the cavitand sensing layer compared to the fluoropolyol layer suggests that COOH containing cavitands layers might be better suited for DMMP sensing than the standard fluoropolyol-sensing layer.

Influence of layer thickness and morphology on sensor responses—The organization of the cavitand layer affects the rate and extent of SPR signal shift because cavities must be accessible to an analyte in order for binding to occur. The literature suggests that spin-coating and LB deposition of cavitand result in similarly structured cavitand layers. Shenoy and co-workers have shown that the SPR response to self-assembled monolayers of methylene-bridged cavitands is similar to that of spin-cast layers of the same cavitand, after normalization for layer thickness (Feresenbet et al. *Sensor Lett.* 2004, 2, 186-193). Hassan and co-workers found that LB films and spin-cast films of an amphiphilic calyx-4-resorcinarene with comparable thickness produced similar SPR responses to toluene vapor (Hassan et al. *Materials Science and Engineering C* 1999, 8-9, 251-25).

Figure 16:
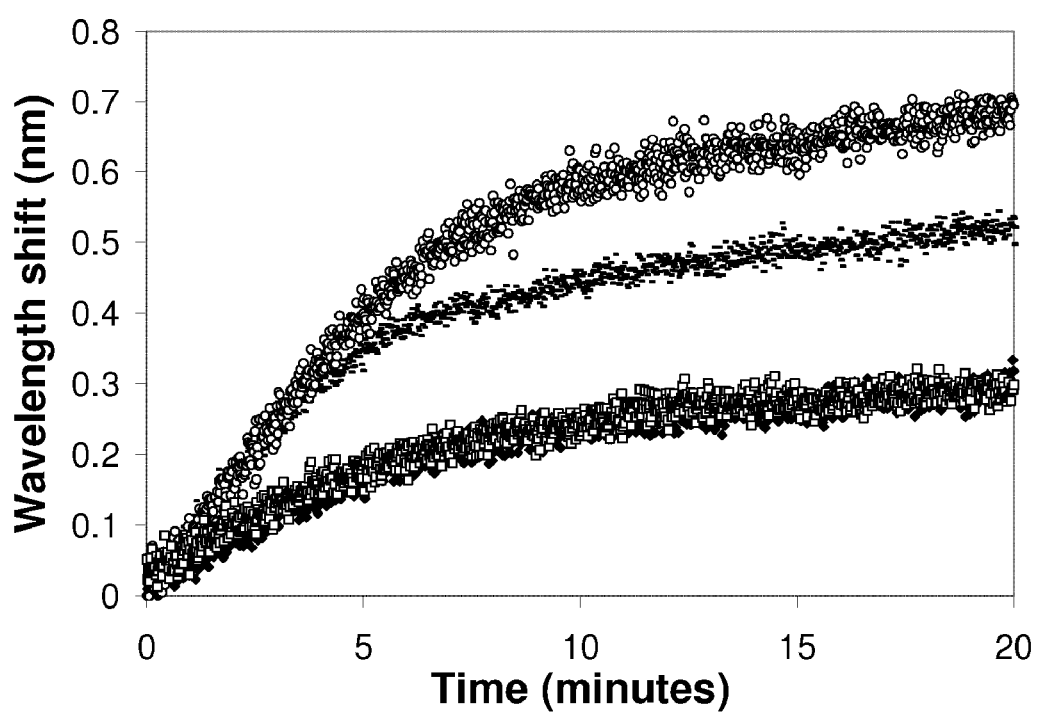
FIG. 16 shows the SPR wavelength shift upon exposure of either a spin-cast film (diamonds), an LB deposited bilayer (open squares), four LB deposited layers (dashes), or eight LB deposited layers (open circles) of COOH-out to a 4.475 ppm concentration of DMMP

Two, four or eight cavitand layers were deposited onto the hydrophilic gold surface such that the final layer had its head group pointing away from the gold surface. The thickness of the bilayer matched that of the spin-cast films. The four and eight layer LB depositions produced films that were two or four time thicker than the spin-cast film. FIG. 16 shows the kinetics of DMMP interaction with the three LB deposited layers of different thickness. Each of these LB deposited layers was formed from a tightly packed cavitand monolayer at the air-water interface. DMMP interaction with the COOH-out, LB bilayer was similar to its interaction with the spin-cast film of COOH-out. Langmuir-Blodgett deposition of cavitand onto the gold surface allows for control over the number of layers and the packing density of the cavitand layers.

The rate and extent of DMMP interaction with the layers increased with layer thickness as shown in FIG. 16. Although the thicker layer was more sensitive to DMMP, it is important to realize that increasing the layer thickness can also result in increased dispersion interaction between the tails of the cavitands and alkane or alcohol contaminants. Nonetheless, the thickest layers were still relatively thin compared to the coatings used with QCM sensors. As the film thickness is doubled, the amount of cavitand on the surface should also double. Hence, the amount of material on the surface can be exploited to determine the effects of diffusion of analyte through the cavitand film. If diffusion through the film is more rapid than the rate of cavitand-analyte complexation, then the rate of SPR shift per molecule should not vary with film thickness. The rate tabulation in Table 1 shows that diffusion was not hindered when the number of layers was increased from two to four, however, diffusion likely becomes a factor when the number of layers is again doubled to eight.

TABLE 1

The thickness (nm-cavitand), rate of response (nm-shift/minute) and rate of response normalized by the thickness (nm-shift/minute/nm-cavitand) for spin-cast and Langmuir-Blodgett layers of COOH-out.

| | Thickness (nm) | Rate (Δλ/minute) | Rate/thickness |
|---|---|---|---|
| Spin-cast Cav-1 | 2.2 | 0.037 | 0.02 |
| 2 LB layers Cav-1 | 2.2 | 0.037 | 0.02 |
| 4 LB layers Cav-1 | 4.5 | 0.072 | 0.02 |
| 8 LB layers Cav-1 | 9 | 0.072 | 0.01 |

Figure 17:
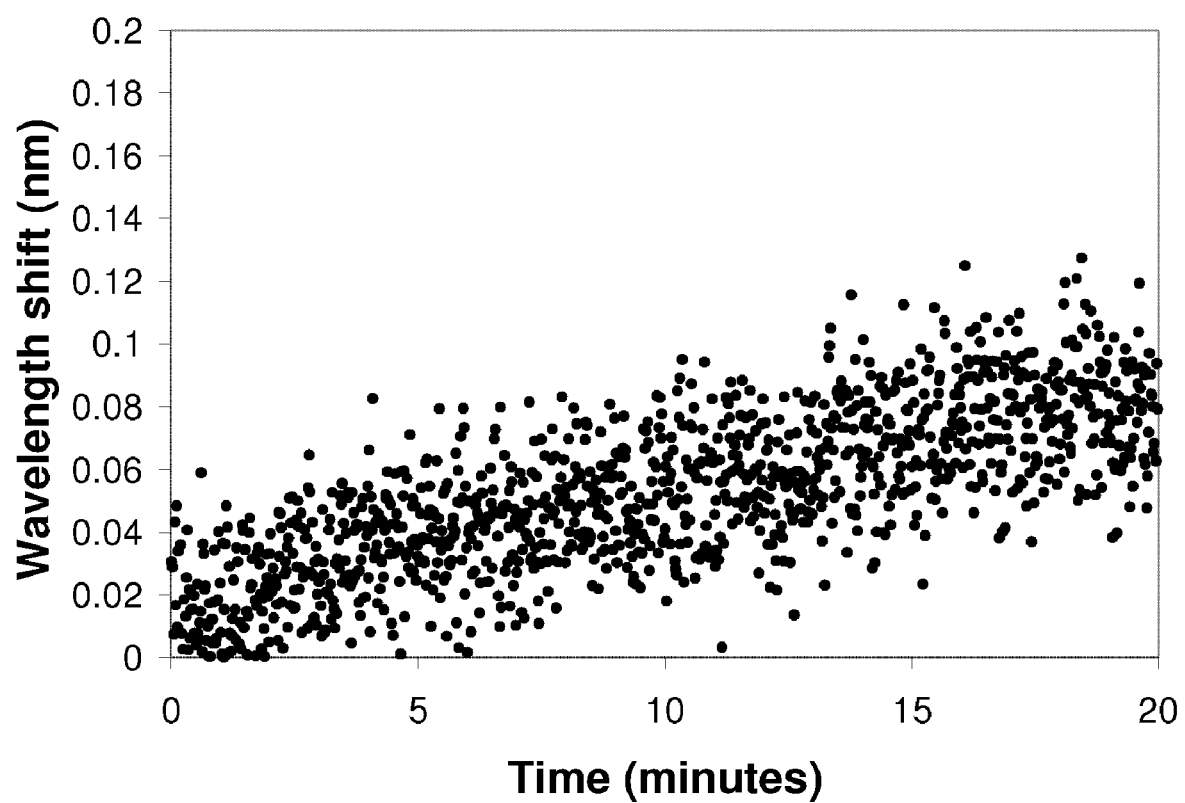
FIG. 17 shows the SPR wavelength shift upon exposure of an eight layer COOH-out LB film to 16 ppb DMMP.

At the 4.475 parts-per-million DMMP concentration studied, the performance of this SPR-based sensor was enhanced by approximately a factor of 2 when the thickness was doubled from a bilayer to four layers of cavitand. Further increase in the layer thickness increased the extent of DMMP sorption by a factor of 1.3 after 20 minutes. Because the thicker LB cavitand layers were more sensitive to DMMP than the thinner spin-cast films, low concentration (ppb) performance of the sensor was examined using the former. For the eight layers LB coated surface, an SPR shift of 0.1±0.04 nm over 20 minutes at a DMMP concentration of 16 ppb was observed, as shown in FIG. 17. Hence, a few layers of cavitand coupled with an SPR transduction scheme can result in a sensor that is very sensitive to the presence of DMMP.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed as new and desired to be protected by Letters Patent of the United States is:

1. A chemical compound consisting of the formula:

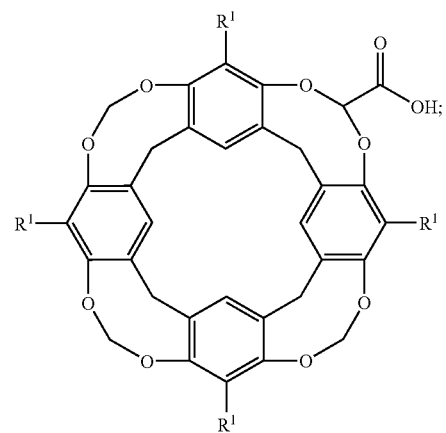

wherein each $R^1$ is independently selected from H and $CH_3$.

2. The chemical compound of claim 1, wherein the compound consisting of the formula:

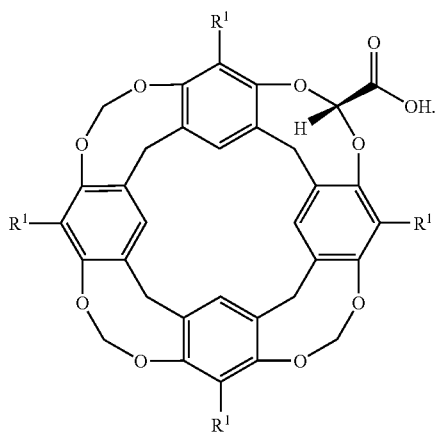

3. The chemical compound of claim 1, wherein the compound consisting of the formula:

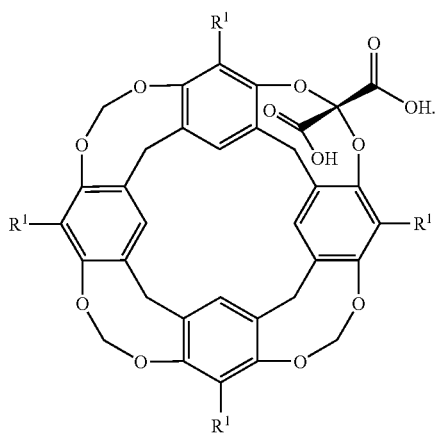

4. The chemical compound of claim 1, wherein each $R^1$ is $CH_3$.

5. A device for detecting an analyte comprising:
a substrate;
a film on the substrate comprising a chemical compound selected from:

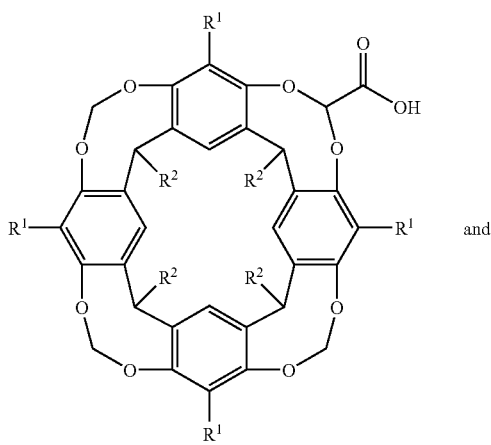

and

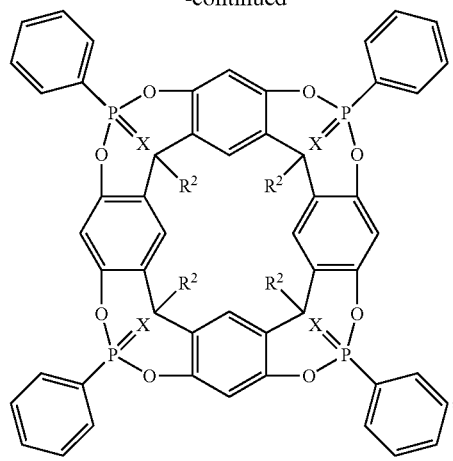

wherein each $R^1$ is an independently selected from H and $CH_3$;
wherein each $R^2$ is an independently selected alkyl group; and
wherein each X is O or S;
a flow cell capable of delivering air suspected of containing the analyte to the film; and
an apparatus capable of measuring the refractive index of the film.

6. The device of claim 5, wherein each $R^1$ is $CH_3$.
7. The device of claim 5, wherein each $R^2$ is $C_5H_{11}$.
8. The device of claim 5, wherein each $R^2$ is $C_{11}H_{23}$.
9. The device of claim 5, wherein each X is O.
10. The device of claim 5, wherein each X is S.
11. The device of claim 5, wherein the apparatus is a surface plasmon resonance apparatus.
12. The device of claim 5, further comprising:
a system capable of correlating a change in the refractive index to the concentration of the analyte.
13. The device of claim 5, wherein the analyte is a chemical warfare agent.
14. The device of claim 5, wherein the analyte is a nerve gas agent, sarin, or dimethyl methyl phosphonate.
15. A method of detecting an analyte comprising:
providing a device comprising:
a substrate;
a film on the substrate comprising a chemical compound selected from:

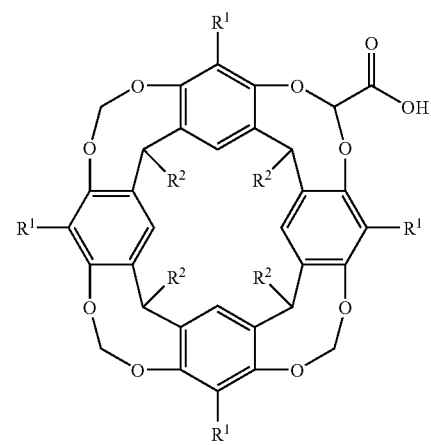

and

-continued

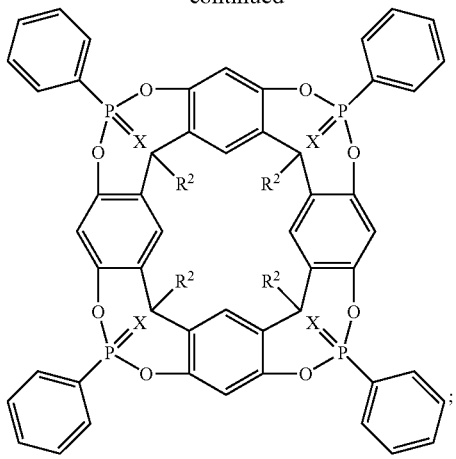

wherein each $R^1$ is an independently selected from H and $CH_3$;

wherein each $R^2$ is an independently selected alkyl group; and wherein each X is O or S;

exposing the film to air suspected of containing the analyte; and measuring a change in the refractive index of the film in response to exposing the film.

16. The method of claim 15, wherein each $R^1$ is $CH_3$.

17. The method of claim 15, wherein each $R^2$ is $C_5H_{11}$.

18. The method of claim 15, wherein each $R^2$ is $C_{11}H_{23}$.

19. The method of claim 15, wherein each X is O.

20. The method of claim 15, wherein each X is S.

21. The method of claim 15, wherein the measuring is performed by a surface plasmon resonance apparatus.

22. The method of claim 15, further comprising:

correlating the change in the refractive index to the concentration of the analyte.

23. The method of claim 15, wherein the analyte is a chemical warfare agent.

24. The method of claim 15, wherein the analyte is a nerve gas agent, sarin, or dimethyl methyl phosphonate.

* * * * *